(12) United States Patent
Trieu

(10) Patent No.: US 7,993,404 B2
(45) Date of Patent: Aug. 9, 2011

(54) TRANSFORMABLE SPINAL IMPLANTS AND METHODS OF USE

(75) Inventor: Hai H Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1297 days.

(21) Appl. No.: 11/392,030

(22) Filed: Mar. 29, 2006

(65) Prior Publication Data

US 2007/0270953 A1    Nov. 22, 2007

(51) Int. Cl.
*A61F 2/44*    (2006.01)
(52) U.S. Cl. ..................................... 623/17.12
(58) Field of Classification Search ............... 623/17.12, 623/17.11; 206/568
See application file for complete search history.

(56) References Cited

U.S. PATENT DOCUMENTS

| | | | | |
|---|---|---|---|---|
| 3,737,027 A * | 6/1973 | Ball | | 206/219 |
| 3,756,389 A * | 9/1973 | Firth | | 206/219 |
| 4,291,799 A * | 9/1981 | Bower, Jr. | | 206/219 |
| 4,462,224 A * | 7/1984 | Dunshee et al. | | 62/530 |
| 4,808,006 A * | 2/1989 | Kaufeler | | 366/332 |
| 5,374,456 A * | 12/1994 | Matossian et al. | | 427/570 |
| 5,437,669 A * | 8/1995 | Yuan et al. | | 606/278 |
| 5,571,189 A | 11/1996 | Kuslich | | |
| 5,888,220 A | 3/1999 | Felt et al. | | |
| 6,248,131 B1 | 6/2001 | Felt et al. | | |
| 6,428,576 B1 | 8/2002 | Haldimann | | |
| 6,443,988 B2 | 9/2002 | Felt et al. | | |
| 6,899,713 B2 * | 5/2005 | Shaolian et al. | | 606/262 |
| 6,932,843 B2 | 8/2005 | Smith et al. | | |
| 6,964,667 B2 | 11/2005 | Shaolian et al. | | |
| 7,004,971 B2 | 2/2006 | Serhan et al. | | |
| 2002/0144392 A1 * | 10/2002 | John et al. | | 29/600 |
| 2002/0147497 A1 | 10/2002 | Belef et al. | | |
| 2004/0102774 A1 | 5/2004 | Trieu | | |
| 2004/0133280 A1 | 7/2004 | Trieu | | |
| 2004/0230309 A1 | 11/2004 | DiMauro et al. | | |
| 2004/0254583 A1 * | 12/2004 | McKay et al. | | 606/99 |
| 2005/0080489 A1 * | 4/2005 | Estes et al. | | 623/17.16 |
| 2005/0197702 A1 * | 9/2005 | Coppes et al. | | 623/17.12 |
| 2005/0203206 A1 | 9/2005 | Trieu | | |
| 2006/0004358 A1 | 1/2006 | Serhan et al. | | |
| 2006/0004456 A1 | 1/2006 | McKay | | |
| 2006/0046961 A1 | 3/2006 | McKay | | |
| 2006/0241766 A1 * | 10/2006 | Felton et al. | | 623/17.12 |
| 2006/0271196 A1 | 11/2006 | Saal et al. | | |
| 2007/0270953 A1 | 11/2007 | Trieu | | |

FOREIGN PATENT DOCUMENTS

WO    WO 2004016205 A2 *    2/2004

* cited by examiner

*Primary Examiner* — Thomas C Barrett
*Assistant Examiner* — David W Bates

(57) ABSTRACT

The present application is directed to transformable implants for a variety of medical applications. The implants transform from a malleable pre-filled article into a more rigid device via hardening of the implant material. The malleable aspects of the implants facilitate delivery and insertion for implantation in a minimally invasive procedure. The hardened implants provide for load-bearing that maximizes in vivo performance. Activation for hardening the implant material may be accomplished by various means, and may occur prior to insertion into the patient, during insertion into the patient, or after insertion into the patient.

57 Claims, 13 Drawing Sheets

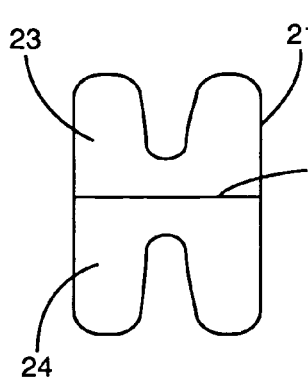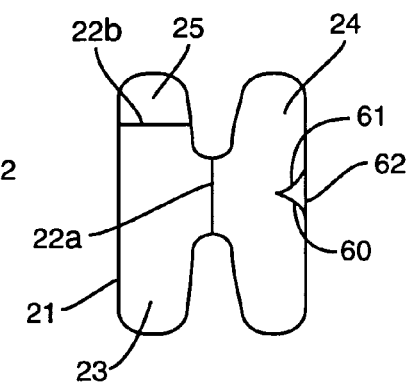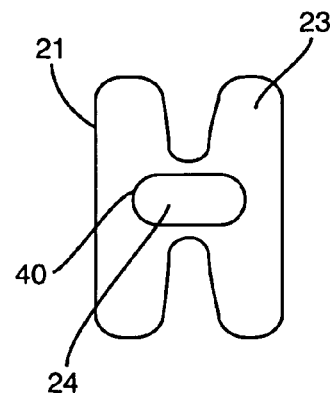
*FIG. 2*          *FIG. 3*          *FIG. 4*
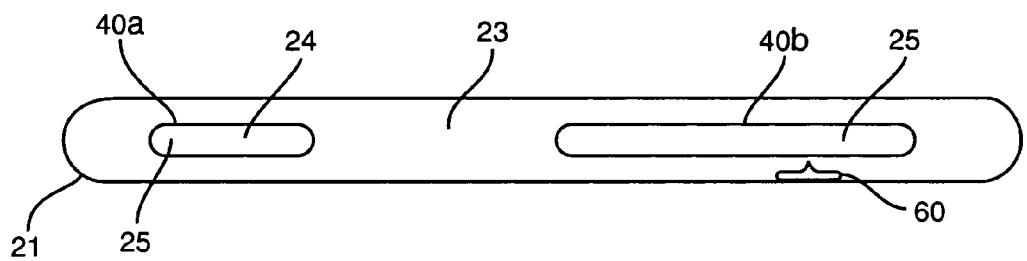
*FIG. 5*
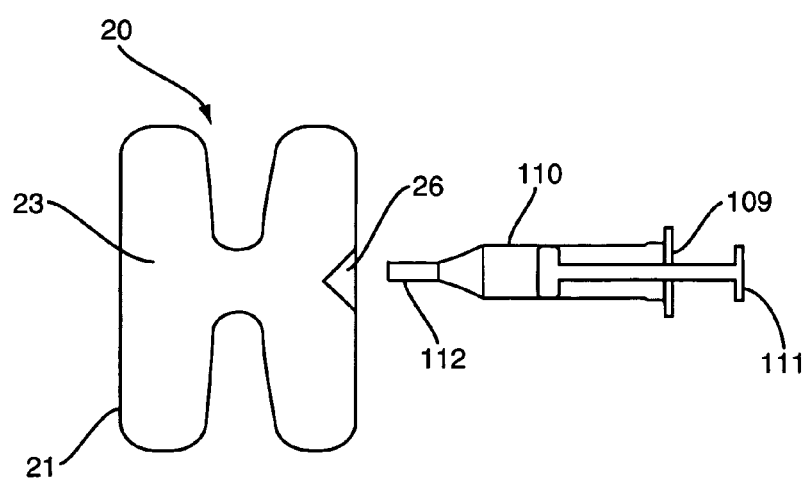
*FIG. 6*

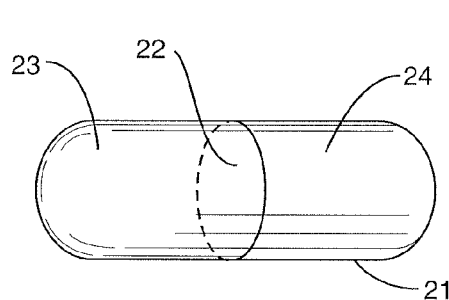
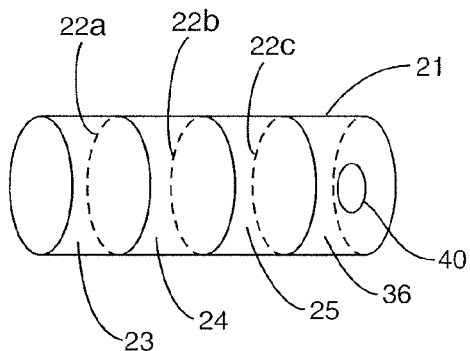
FIG. 15  FIG. 16
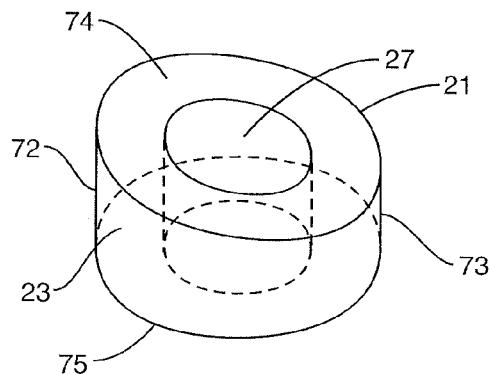
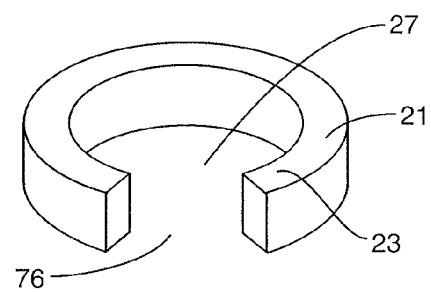
FIG. 17  FIG. 18
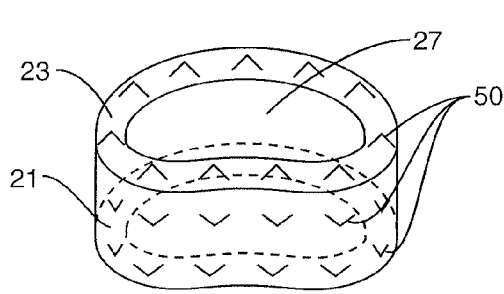
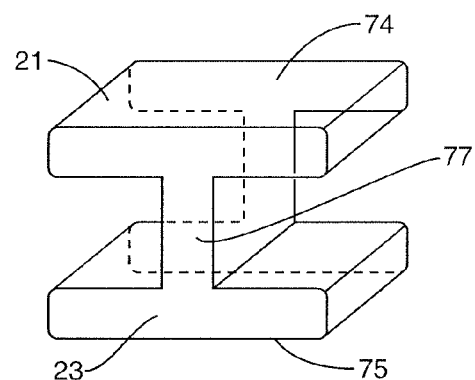
FIG. 19  FIG. 20

TRANSFORMABLE SPINAL IMPLANTS AND METHODS OF USE

BACKGROUND

The present application is directed to implants and methods for a variety of medical applications and, more specifically, to implants that transform from a malleable state for insertion and positioning within a patient to a hardened load bearing state after being positioned within the patient.

There are numerous devices and methods for inserting an implant within a patient to support a vertebral member. Many of these generally involve invasive surgery that requires resecting tissue in order to gain access to the injury site. This may include the need to cut through skin, nerves, vessels, muscles, ligaments, and/or tendons. These procedures may also require longer surgical procedures that use general or spinal anesthesia, and blood transfusions.

Invasive surgery may also result in a longer hospitalization period that is necessary for the patient to recover. During this time, the patient may have post-surgical pain and discomfort. Further, there may be a need for significant recovery time that requires physical therapy. Inherent with this amount of additional care is the increased costs associated therewith.

SUMMARY

The present application is directed to implants and methods of use for supporting one or more vertebral members. The implant may include a flexible shell that contains a precursor material. In an initial state, the material and shell may be malleable for insertion into the patient. The precursor material may be activated and begin to cure to a hardened state. The hardening may occur by polymerization, crosslinking, complexation, or gelation. The implant may be inserted into the patient while still in a malleable state. The implant is positioned within the patient and cures to a hardened load-bearing state to support one or more of the vertebral members. The activation of the precursor material may occur prior to insertion into the patient, during insertion into the patient, or after insertion into the patient.

BRIEF DESCRIPTION OF THE DRAWINGS

FIG. 2 is a side schematic view illustrating an implant according to one embodiment.

FIG. 3 is a side schematic view illustrating an implant according to one embodiment.

FIG. 4 is a side schematic view illustrating an implant according to one embodiment.

FIG. 5 is a side schematic view illustrating an implant according to one embodiment.

FIG. 6 is a side schematic view illustrating an implant and a syringe according to one embodiment.

FIG. 15 is a perspective view illustrating an implant according to one embodiment.

FIG. 16 is a perspective view illustrating an implant according to one embodiment.

FIG. 17 is a perspective view illustrating an implant according to one embodiment.

FIG. 18 is a perspective view illustrating an implant according to one embodiment.

FIG. 19 is a perspective view illustrating an implant according to one embodiment.

FIG. 20 is a perspective view illustrating an implant according to one embodiment.

DETAILED DESCRIPTION

The present application is directed to transformable implants for a variety of medical applications. In one embodiment, the implants include a shell that contains one or more precursor materials. The shell may be constructed of a flexible material and the one or more precursor materials that are flowable resulting in the implant being malleable for implanting into the patient.

The precursor materials undergo an activation process that starts the transformation to a hardened state. The activation process may include chemical reaction, thermal reaction, photo reaction such as visible, ultra-violet, or infrared light, radiation, electrical and physical reactions. The activation process may begin prior to insertion of the implant into the patient, during the insertion, or after insertion.

The transformation of the precursor material or materials to the hardened state may occur through crosslinking, polymerization, gelation, complexation, and others. The transformation causes the implant to change from a malleable device that facilitates insertion and positioning with the patient, to a rigid or semi-rigid load bearing device. The term "hardened" and the like refers to materials and combination of materials that can solidify, in situ, at the tissue site, in order to retain a desired load bearing position and configuration.

The implants may be applicable to a variety of medical operations. One application includes an intervertebral device such as a nucleus replacement, disc replacement, or fusion device. A vertebral rod or plate that extends along one or more vertebral members is another application. The implants may also be used for an interspinous spacer.

Figure 1A:
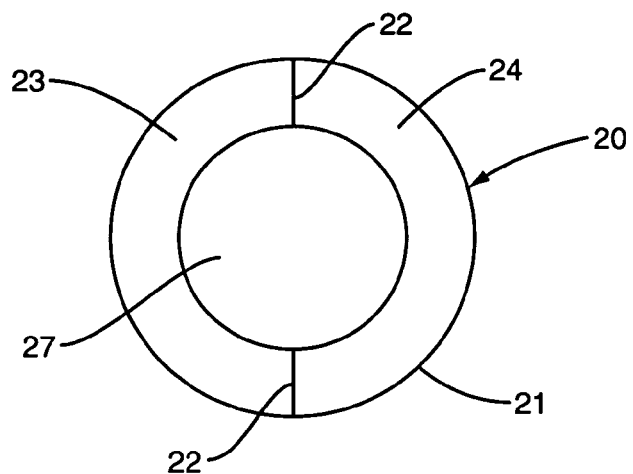
FIG. 1A is a top schematic view illustrating an implant according to one embodiment.

FIGS. 1A-1E illustrates one method of implementation of an implant 20. FIG. 1A illustrates the implant 20 including a shell 21 and seals 22 that physically divide the shell 21 into first and second chambers 23, 24 that are physically isolated. A first precursor material is contained within the first chamber 23 and segregated from a second material that is contained in the second chamber 24. The seals 22 physically segregate the precursor materials and prevent activation. The shell 21 is constructed of a flexible material and may have a predefined shape, or may be amorphous. In this embodiment, shell 21 has an annular predefined shape. Prior to activation, the implant 20 is malleable and may be deformed from the predefined shape for insertion into and positioning within the patient.

Figure 1B:
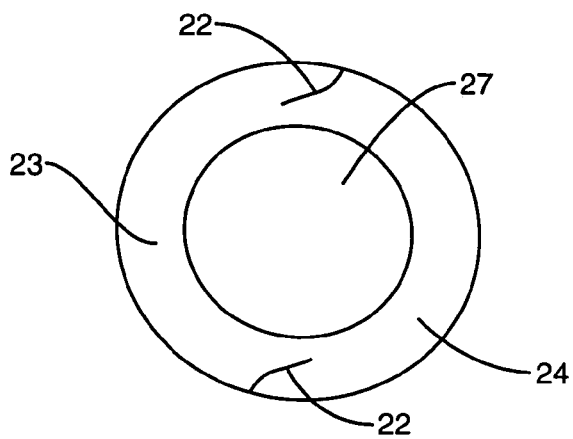
FIG. 1B is a top schematic view illustrating an implant according to one embodiment.

FIG. 1B illustrates the seals 22 being compromised causing the materials to mix together and being the activation. One manner of compromising the seals 22 includes physically deforming the shell 21 which may build pressure within one or more of the chambers 23, 24 to rupture the seals 22. The materials may mix together themselves, or mixing may be aided by deforming and kneading the shell 21 thereby forcing the materials throughout the entirety of the interior space previously formed by the two chambers 23, 24.

Figure 1C:
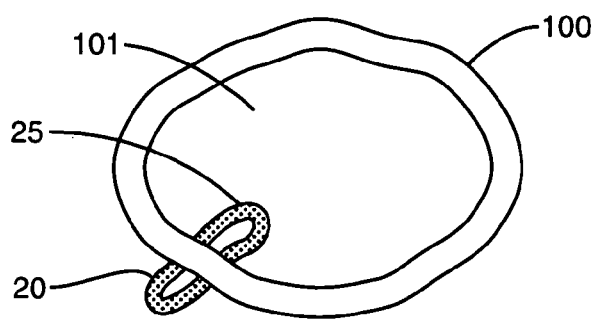
FIG. 1C is a top schematic view illustrating an implant being inserted into an annulus fibrosis according to one embodiment.

The mixed materials remain sufficiently viscous for a predetermined time after activation for the implant to remain malleable for insertion and positioning. The embodiment of FIG. 1C illustrates the implant 20 being inserted through the annulus fibrosis 100 and into an interior space 101 of an intervertebral disc. The malleable nature of the implant 20 upon activation allows for the shell 21 to be deformed into a reduced width for insertion through the annulus fibrosis. During the insertion process, the materials may begin to polymerize and solidify. The implant 20 remains malleable during the initial polymerization and solidification.

Figure 1D:
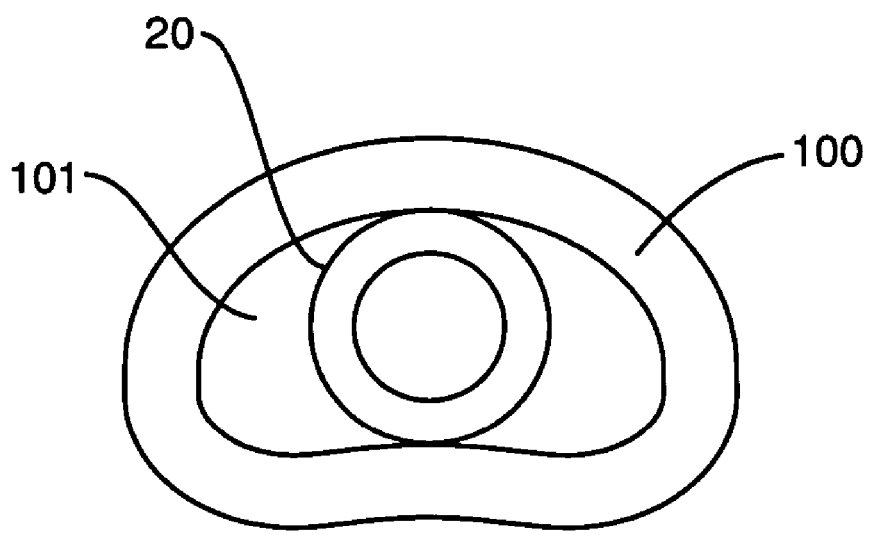
FIG. 1D is a top schematic view illustrating an implant positioned within an interior disc space according to one embodiment.
Figure 1E:
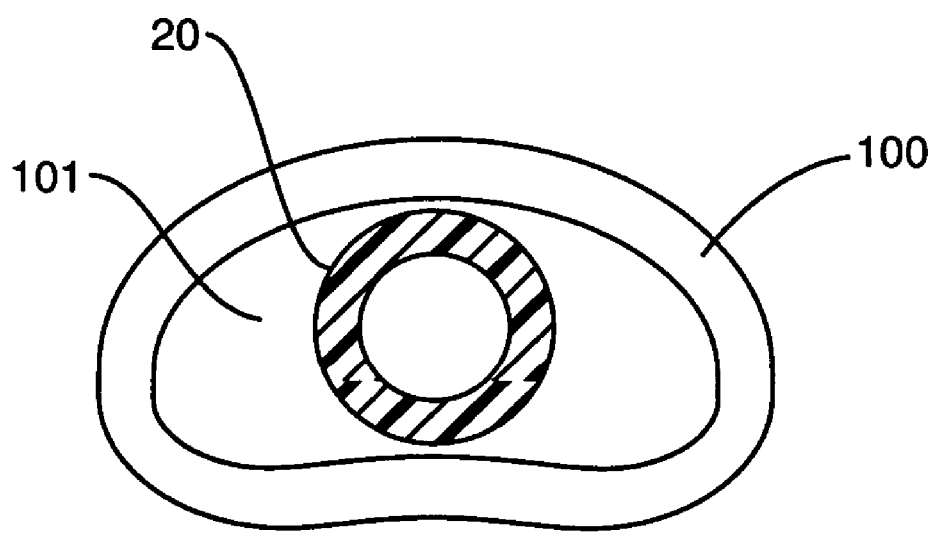
FIG. 1E is a top schematic view illustrating an implant positioned within an interior disc space according to one embodiment.

After insertion through the annulus fibrosis 100, the shell 21 returns towards the predefined shape which in this embodiment is an annular ring as illustrated in FIG. 1D. The shell 20 is moved to the appropriate position within the interior space 101 as the materials continue to transform towards a hardened state. The amount of hardening increases with time as the materials transform to a lower viscosity. The materials eventually transform to a hardened load-bearing state for supporting the adjacent vertebral members. In one embodiment, the materials go through a phase transition and assume a rigid, solid state as illustrated in FIG. 1E. In other embodiments, the materials harden to a semi-rigid state that is also able to support the vertebral members.

The shell 21 may constructed of a variety of materials. Examples include but are not limited to various polymeric materials, such as aliphatic or aromatic polycarbonate-based and non-polycarbonate-based polyurethanes, polyethylene terephthalates, polyolefins, polyethylene, polycarbonate, ether-ketone polymers, polyurethanes, nylon, polyvinyl chloride, acrylic, silicone, and combinations thereof. The material comprising the shell 21 may further be reinforced with woven or non-woven textile materials. Examples of suitable reinforcement materials include those that are polymeric and metallic in nature.

In one embodiment, the shell 21 is constructed from a single layer. The layer may be constructed of a common material throughout, or may be constructed of two or more different materials. Shell 21 may also be constructed of multiple layers. The entire shell 21 may include multiple layers, or a limited section may include multiple layers. In one embodiment, shell 21 includes an inner layer that is encased in fabric. In one embodiment, the shell 21 includes an insertion section that is initially inserted into the patient. By way of example and using FIG. 1C as an example, insertion section 25 is introduced into the patient and through the annulus fibrosis 100 prior to the remainder of the shell 21. The insertion section 25 may be reinforced because of the extra wear. The reinforcement may include multiple layers, textile materials, and the like.

A variety of different precursor materials may also be used in the various embodiments. In some embodiments, a single precursor material is positioned within the shell 21 and upon activation changes to the hardened state. In other embodiments, two or more precursor materials are activated. The precursor material or materials should be flowable and include a viscosity for the implant 20 to be malleable prior to the material reaching a predetermined hardened state. This facilitates insertion and positioning of the implant 20 within the patient in a minimally invasive manner. The material or materials should further be curable in situ, at the tissue site, to undergo a phase or chemical change sufficient to retain a desired position and shape and assume a load-bearing capacity.

The precursor material and materials may range from an injectable liquid to a visco-elastic solid. In one embodiment, the material cures to a hardened state within about 2 minutes to about 6 hours after activation. In a specific embodiment, the material cures in between about 5 to about 60 minutes after activation.

The material may further be homogeneous with the same chemical and physical properties throughout, or heterogeneous. A variety of materials may be used and may include silicones, polyurethanes, silicone-polyurethanes, polyvinyl chlorides, polyethylenes, styrenic resins, polypropylene, polyolefin rubber, PVA, protein polymers, thermoplastic polyesters, thermoplastic elastomers, polycarbonates, acrylonitrile-butadiene-styrene resins, acrylics, nylons, styrene acrylonitriles, cellulosics, DBM, PMMA bone cement, tissue growth factor, epoxy, calcium phosphate, calcium sulfate, and resorbable polymers such as PLA, PLDLA, and POLYNOVO materials. Various materials are disclosed in U.S. Pat. Nos. 5,888,220 and 6,428,576, and U.S. Patent Application Nos. 2004/0230309, 2004/0102774, 2006/0004456, and 2004/0133280, each of which is herein incorporated by reference in their entirety. The material may also include a pharmaceutical composition comprising one or more biological response modifiers. Examples of pharmaceutical compositions are disclosed in U.S. Patent Application No. 2006/0046961 herein incorporated by reference in its entirety. The material may further include an opaque additive, such as barium sulfate, that will be visible on an X-ray.

One or both of the shell 21 and material may be bioresorbable. In one embodiment, the shell 21 is a bioresorbable non-porous (sheet or film) or a bioresorbable porous (braided fibers) shell. The material is a precursor of resorbable polymer that polymerizes, cures or crosslinks in situ. The following families of resorbable polymers can be used for the shell 21 and/or the filling materials: poly(L-lactic acid), poly(D,L-lactic acid), poly(D L-lactic-co-glycolic acid), poly(glycolic acid), poly(epsilon-caprolactone), polyorthoesters, polyanhydrides, polyhydroxy acids, polydioxanones, polycarbonates, polyaminocarbonates, polyurethane, poly(ethylene glycol), poly(ethylene oxide), partially or fully hydrolyzed poly(vinyl alcohol), poly(ethylene oxide)-co-poly(propylene oxide) block copolymers (poloxamers and meroxapols), poloxamines or combinations thereof.

Activation of the material or materials may occur by a variety of methods. In one embodiment, the activation may start before the implant 20 is inserted into the patient. The implant 20 is activated and during the activation is inserted and positioned within the patient while still malleable and prior to reaching the hardened state. The implant 20 may also be activated during the insertion process. The activation may occur during the deformation necessary to insert the implant 20 into the patient, such as the necessary compression during insertion through a cannula in a minimally invasive procedure. Activation may also occur after the implant 20 is inserted within the patient. In one embodiment, the implant 20 is inserted and accurately positioned prior to activating the material or materials.

Activation methods may further include exposing the implant with the one or more materials 23, 24 to an energy source prior to insertion into the patient. The energy source may include a thermal source, such as a heat gun or autoclave chamber. The energy source may also include a radiation source such as an X-ray device or fluoroscopy arm. An electrical source may further be used such as a battery or source that emits AC or DC electrical current. Light energy including ultraviolet or infrared light sources may be used for activation. Activation in other embodiments may be caused by a physical energy source such as pressure or impact force that is applied to the implant 20.

One method of activation occurs by physically mixing two or more precursor materials that are already contained within the shell 21. FIG. 1B illustrates an embodiment with the shell 21 including first and second chambers. One or more seals 22 are broken to allow the materials 23, 24 to physically mix together. Mixing may occur by kneading the shell 21 prior to insertion, during the compression and deformation for insertion into the patient, or after insertion. FIG. 2 illustrates another embodiment with a single seal 22 physically separating the chambers 23, 24. FIG. 3 illustrates a first seal 22a that forms first and second chambers 23, 24 for physically separating the first and second materials. A rupture device 60 is positioned within the shell 21 to break the seal 22a. Rupture device 60 may include an edge 61 that is brought into contact to rupture the seal 22a. In one embodiment, a base 62 of the rupture device 60 is attached to the inner wall of the shell 21. This positioning maintains the edge 61 facing outward towards an interior of the shell 21 to lessen the likelihood of inadvertently rupturing the shell 21. The material surrounds and covers the rupture device after hardening to prevent any potential damage from occurring.

The shape and sizes of the various chambers may vary depending upon the materials. FIG. 1A illustrates an embodiment with first and second chambers 23, 24 that are substantially equal in size. FIG. 3 illustrates first and second chambers 23, 24 that are substantially equal. Shell 21 further includes a second seal 22b that forms a third chamber 25. The third chamber 25 is considerably smaller than either of the first two chambers 23, 24. In the embodiment of FIG. 3, the second seal 22b may be ruptured by a variety of manners, including physically manipulating the shell 21. Physically separating the precursor materials may include placing one or more of the materials within a container 40 positioned within the shell 21. FIG. 4 illustrates an embodiment with a container 40 positioned within the shell 21. Container 40 forms an enclosed area sized to hold the second material in physical separation from the first material within the first chamber 23. The container 40 may be statically positioned within the shell 21, or may move (i.e., float) throughout the first chamber 23. Rupturing of the container 40 may occur in a variety of methods, including physical manipulation of the shell 21, or contact with an edge 61 (not illustrated). Container 40 may be made from the same materials as previously described for the shell 21. The container 40 may be constructed to be weaker than the shell 21 due to thinner or weaker walls. The weaker construction ensures that upon activation, the containers 40 can be ruptured without rupturing the shell 21.

The number of separate containers 40 within the shell 21 may vary. FIG. 4 illustrates a single container 40 within the shell 21. FIG. 5 illustrates the shell 21 that forms a rod and includes first and second containers 40a, 40b. The shell 21 forms a first chamber 23, with the first container 40a forming a second chamber 24 and the second container 40b forming a third chamber 25. Multiple containers 40 may be the same size or different sizes such as illustrated in FIG. 5 with the second container 40b being larger than the first container 40a. In this embodiment, a rupture device 60 is attached to the shell 21 to rupture one or both of the containers 40a, 40b.

Physical segregation may further include injecting one or more of the precursor materials into the shell. FIG. 6 illustrates a shell 21 including a single chamber 23 that contains a first precursor material. Shell 21 includes an inlet 26 for introducing additional materials and prevents the escape of material that is within the chamber 23. A second precursor material is introduced into the chamber 23 through a syringe 109. The syringe 109 includes a barrel 110 sized to contain a predetermined amount of the second precursor material. A plunger 111 fits within the barrel 110 and forces the second material through a port 112. In use, the second material is placed within the barrel 110 either through introduction via the port 112 or through a proximal end of the barrel 110. The port 112 is inserted through the inlet 26 and into the chamber 23. The plunger 111 is depressed in a distal direction to force the second material from the barrel 110 and through the port 112 into the chamber 23. Markings on the barrel 110 may indicate the amount of second material that is expelled through the port 112. The introduction of the second material 24 begins the activation, which may further include additional physical manipulation of the shell 21 for full mixing.

Figure 7:
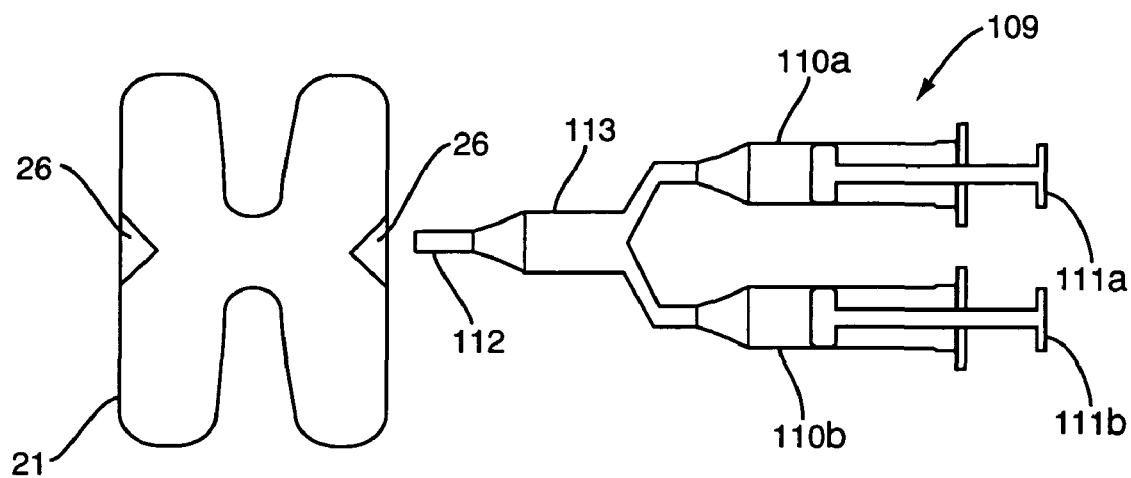
FIG. 7 is a side schematic view illustrating an implant and a syringe according to one embodiment.

The syringe 109 may further include two or more separate barrels 110. FIG. 7 illustrates a syringe 109 with first and second barrels 110a, 110b that are physically separated and each sized to contain one of the first and second materials. A plunger 111a, 111b positioned within each barrel 110a, 110b forces the materials 23, 24 into a mixer 113 where the materials are mixed together. A port 112 is positioned on the distal end of the mixer 113 for insertion into the inlet 26. In one embodiment, the chamber 23 is initially empty with the body 21 assuming a predefined shape which in this instance is an interspinous spacer. In some embodiments, multiple inlets 26 are positioned within the body 21 for introducing the materials.

Various notification methods may be used to indicate to the physician that activation has occurred. In one embodiment, the implant 20 becomes less malleable as the material or materials begin to cure and harden. The physician is able to tactilely feel this change and confirm activation. In one embodiment, the shell 21 is constructed of a translucent or transparent material. The precursor material or materials may change color upon activation. In one example, activation by an energy or electrical source causes the material or materials to change color. This change can be visually noticed by the physician. In one embodiment that includes mixing of two or more precursor materials, the materials may each have a separate color and mixing can be visually identified. In one embodiment, the mixed materials may change color. By way of example, a first precursor material may be blue and a second precursor material may be yellow. These two materials can be distinguished while physically separated. Upon mixing and activation, the mixed materials change to a green color. Visual and tactile indication may also be used to ensure that the precursor materials are fully mixed.

The transformable implant 20 may be used in a variety of different medical contexts. FIGS. 1A-1E illustrates one embodiment for nucleus replacement of an intervertebral disc. In one embodiment, the implant 20 includes an annular shell 21 with a central opening 27. The implant 20 is malleable prior to and during an initial period of activation to be deformed and fit within an opening in the annulus fibrosis 100.

Figure 8:
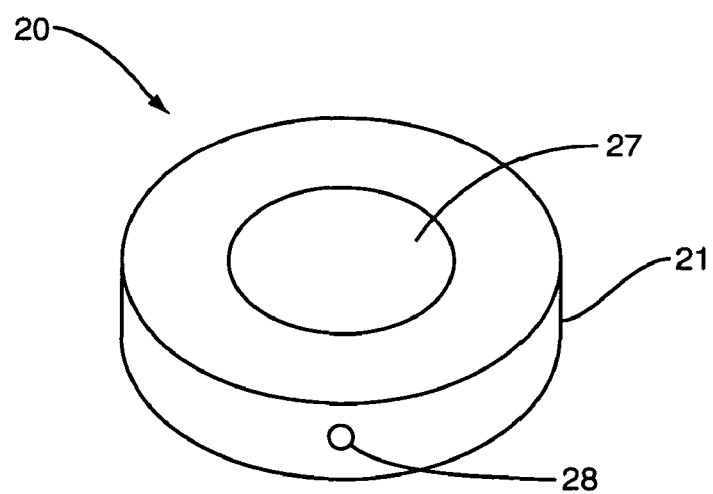
FIG. 8 is a perspective view illustrating an implant according to one embodiment.

FIG. 8 illustrates another embodiment of a nucleus replacement implant 20. The implant 20 includes an annular shell 21 with an opening 27. A conduit 28 extends through the shell 21 and into the opening 27 for introduction of filler material. Any suitable osteogenic material or composition is contemplated for the filler material, including autograft, allograft, xenograft, demineralized bone, and synthetic and natural bone graft substitutes, such as bioceramics and polymers, and osteoinductive factors. The terms osteogenic material or osteogenic composition used herein broadly include any material that promotes bone growth or healing including autograft, allograft, xenograft, bone graft substitutes and natural, synthetic and recombinant proteins, hormones and the like. Filler material is further disclosed in U.S. Patent Application Publication No. 2004/0102774 herein incorporated by reference in its entirety.

Figure 9:
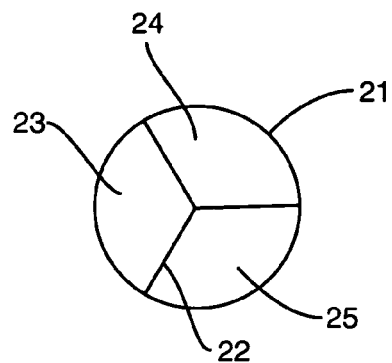
FIG. 9 is a schematic view illustrating an implant according to one embodiment.
Figure 10:
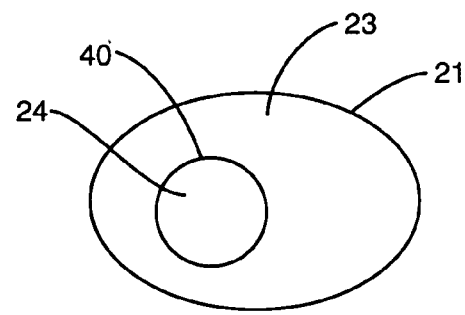
FIG. 10 is a schematic view illustrating an implant according to one embodiment.
Figure 11:
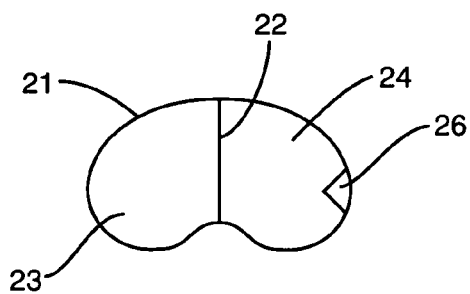
FIG. 11 is a schematic view illustrating an implant according to one embodiment.
Figure 12:
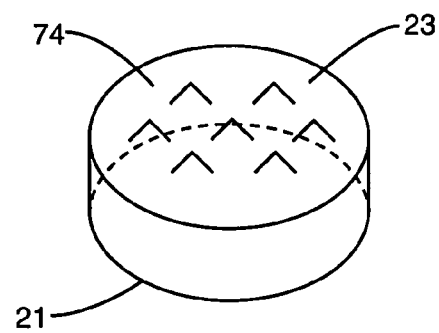
FIG. 12 is a perspective view illustrating an implant according to one embodiment.
Figure 13:
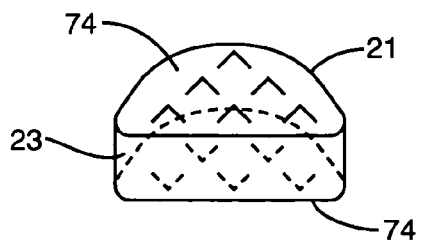
FIG. 13 is a perspective view illustrating an implant according to one embodiment.
Figure 14:
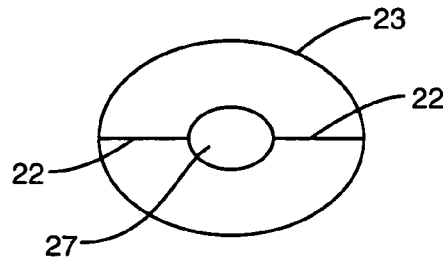
FIG. 14 is a top schematic view illustrating an implant according to one embodiment.

The transformable implant 20 may also be used for full disc replacement following a discetomy or replacement of vertebral member and disc following a corpectomy. The implants 20 may include a variety of shapes and sizes depending upon the specific context of use. FIG. 9 illustrates a spherical shell 21 including a seal 22 that divides the interior into three chambers 23, 24, 25 to physically segregate materials. FIG. 10 illustrates an oblong shell with a container 40 for segregating the materials into the first and second chambers 23, 24. FIG. 11 illustrates an elongated shell 21 having a kidney shape that conforms to the shape of the adjacent vertebral members. This embodiment features first and second chambers 23, 24 formed by a seal 22 with an inlet 26 that leads into the second chamber 24. In one embodiment, first and second materials are contained in the chambers 23, 24, and a third material is introduced through the inlet 26. FIG. 12 includes a disc shape shell 21 with a semi-disc or half-disc shell 21 illustrated in FIG. 13. The embodiments of FIGS. 12 and 13 include a single chamber 23 for containing a single precursor material. This material may be activated by non-mixing activation methods. FIG. 14 illustrates an annular shell 21 having a substantially donut shape with a central opening 27 and seals 22 forming two separate chambers 23, 24. FIG. 15 includes a capsule-shaped shell 21 with a single seal 22 forming first and second chambers 23, 24. FIG. 16 includes a cylindrical shell 21 with three separate seals 22a, 22b, 22c forming four chambers 23, 24, 25, 36 and a container 40 positioned within chamber 36. FIG. 17 includes a tapered cylinder shell 21 with the height of a first sidewall 72 being greater than a second sidewall 73. One or both of the superior and inferior surfaces 74, 75 are angled. FIG. 18 illustrates an open-ring shell 21 with a gap 76 that leads into the opening 27. FIG. 19 includes a half-round shell 21 with an opening 27. FIG. 20 includes an I-shape with superior and inferior 74, 75 supported by an intermediate strut 77. The embodiments of FIGS. 17-20 include a single chamber 23 to hold a single precursor material. It is to be understood that the implant 20 may include various other shapes and sizes than those disclosed in these Figures. Additionally, the various embodiments may include various manners of containing the precursor material and materials.

The implant 20 may also be used as a vertbroplasty device. A portion of the vertebral member may be hollowed or otherwise opened using a variety of methods including balloon expansion. The implant 20 may then be inserted into the hollowed section and hardened.

In some embodiments, body 21 includes teeth 50 for preventing expulsion of the implant 20 after insertion. In one embodiment, teeth 50 are positioned about the entirety of the shell 21 as illustrated in FIG. 19. Teeth 50 may also be positioned on limited sections of the shell 21, including the superior and inferior surfaces 74, 75 as illustrated in FIG. 13, and the superior surface 74 in the embodiment of FIG. 12. Teeth 50 may include a variety of shapes and sizes. Teeth 50 may each include the same shape and size, or may comprise a variety of shapes and sizes.

Figure 21A:
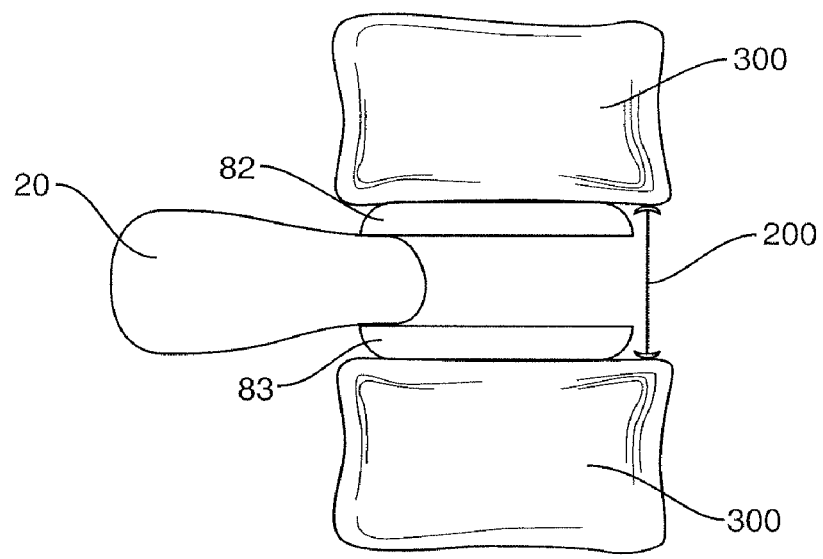
FIG. 21A is a side schematic view illustrating an implant being inserted into a patient according to one embodiment.
Figure 21B:
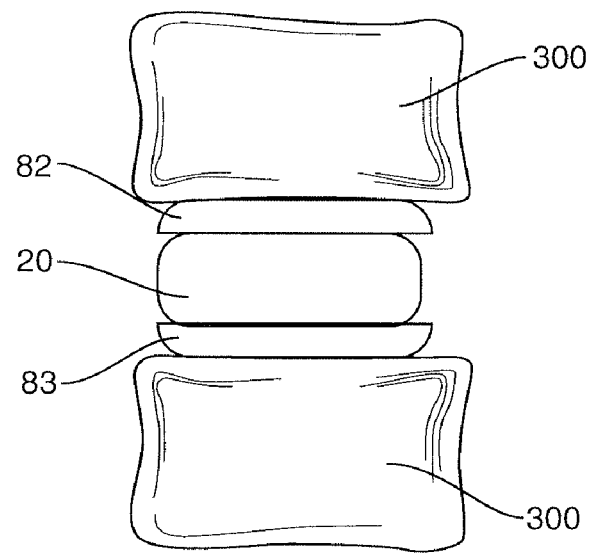
FIG. 21B is a side schematic view illustrating an implant being inserted into a patient according to one embodiment.

Another intervertebral application includes the implant 20 acting as an intermediate support mechanism. FIGS. 21A and 21B illustrate an embodiment with first and second endplates 82, 83 positioned within the intervertebral space formed between adjacent vertebral members 300. A distractor 200 may be positioned to establish a height of the intervertebral space. The first and second endplates 82, 83 may be positioned to contact the vertebral members 300. The implant 20 is inserted while in a malleable state and deformed to fit between the endplates 82, 83. The implant 20 cures to a hardened state to support the members 82, 83 at the desired spacing. The distractor 200 may remain in position to support the vertebral members 300 until the implant 20 cures to a hardened state, or may be removed once the implant 20 is inserted and prior to being completely hardened.

In one embodiment, the insertion of the intervertebral implant 20 into the intervertebral space may cause distraction of the vertebral members. In one embodiment, the material or materials expand during curing to the hardened state to cause distraction.

Figure 22:
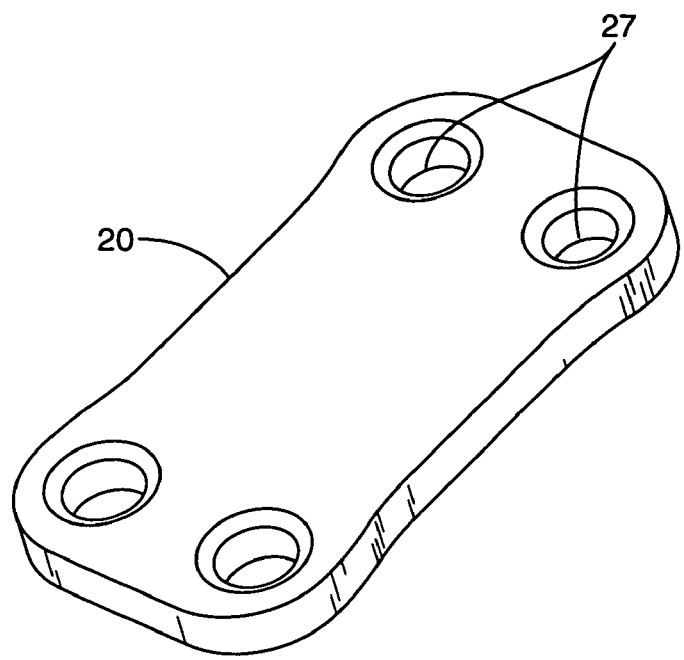
FIG. 22 is a perspective view illustrating an implant according to one embodiment.
Figure 23:
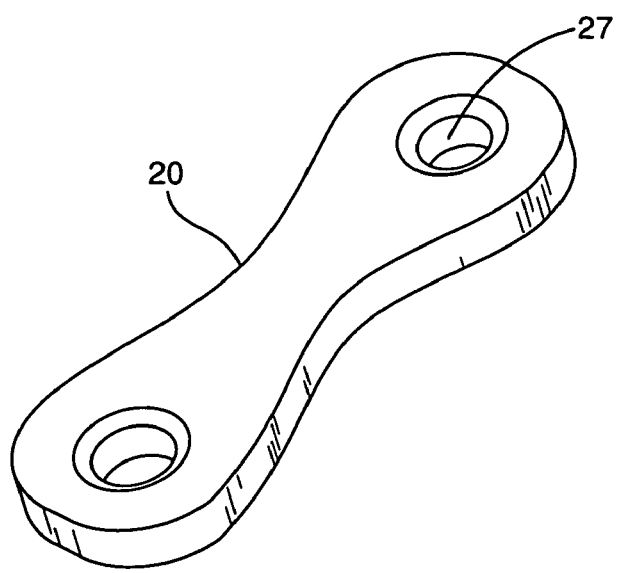
FIG. 23 is a perspective view illustrating an implant according to one embodiment.

Implant 20 may further include a vertebral plate as illustrated in FIGS. 22 and 23. The plates may include a variety of lengths, widths, and thicknesses depending upon the context of use. Openings 27 may further extend through the plates for receiving fasteners for attachment to the vertebral members. The malleable nature of the plates may facilitate insertion in a more minimally-invasive manner than with traditional rigid plates. Further, the malleable nature provides for conforming the plate to the contours of the vertebral members.

Figure 24A:
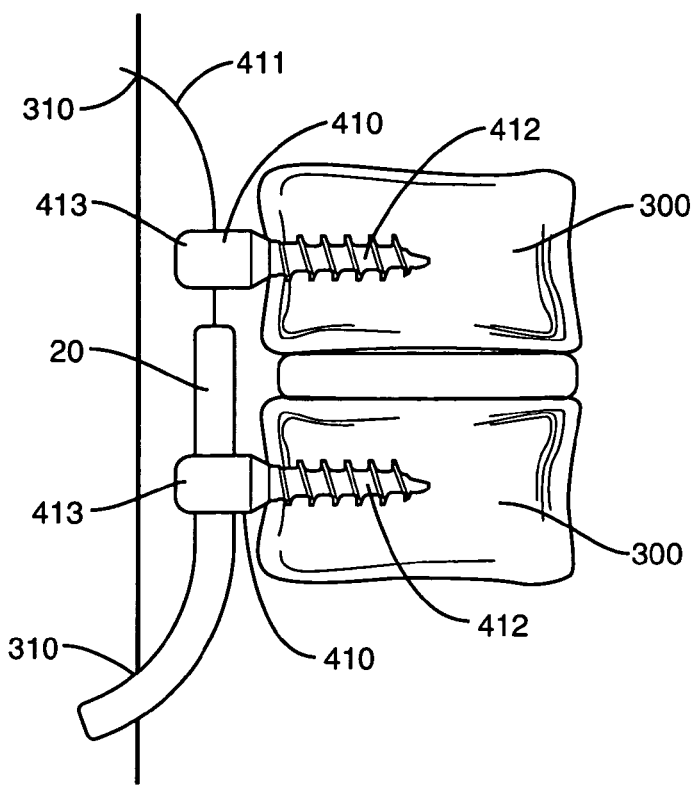
FIGS. 24A and 24B are side schematic views illustrating an implant being inserted into a patient according to one embodiment.
Figure 24B:
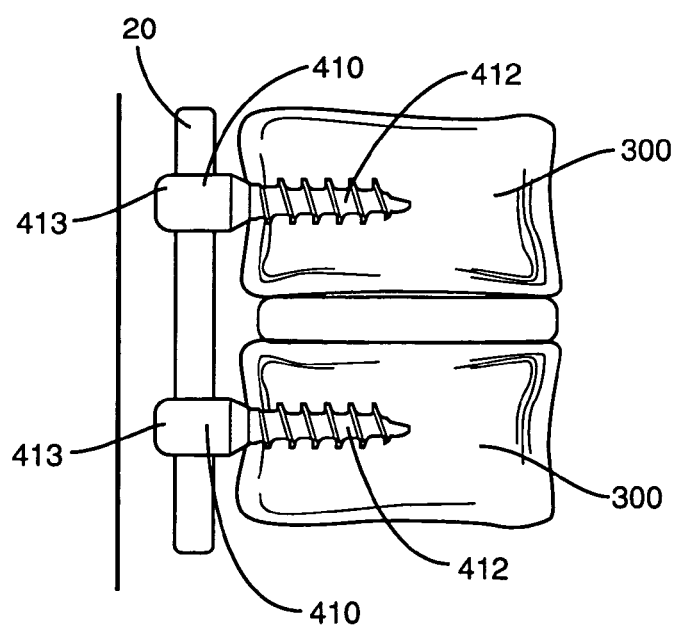

The implant 20 may also be formed as a vertebral rod. The rod may include a variety of lengths and diameters depending upon the use. FIG. 5 illustrates one embodiment of a rod. FIGS. 24A and 24B illustrate one embodiment of inserting and attaching the rod implant 20 to the vertebral members 300. An anchor 410 is mounted to each of the vertebral members 300. Each anchor 410 includes a shaft 412 that extends into the vertebral members 300, and an outwardly-extending head 413. Head 413 may include a saddle with opposing arms forming a channel therebetween that is sized to contain the implant 20. A fastener (not illustrated) may connect within the saddle to maintain the implant 20 within the channel.

FIG. 24A illustrates the implant rod 20 in a malleable state that is bent during insertion through an incision 310. In this embodiment, a guide wire 411 guides the movement of the implant rod 20 during insertion into the patient and into each of the anchors 410. The nature of the material provides for threading the implant rod 20 through each anchor head 413 as illustrated in FIG. 24B. Once at this position, the material cures to a hardened state thus forming a load-bearing support for the vertebral members 300.

Figure 25:
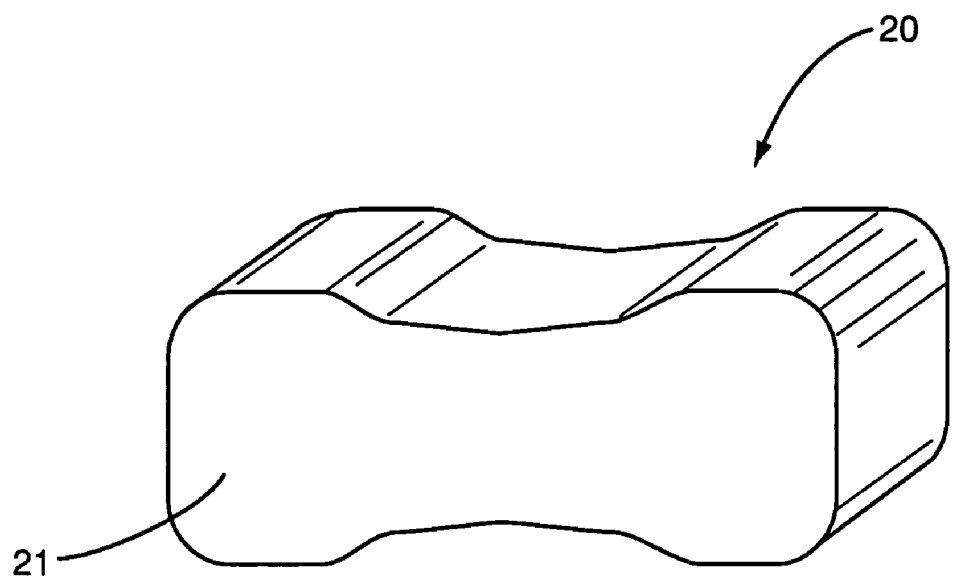
FIG. 25 is a perspective view illustrating an implant according to one embodiment.
Figure 26:
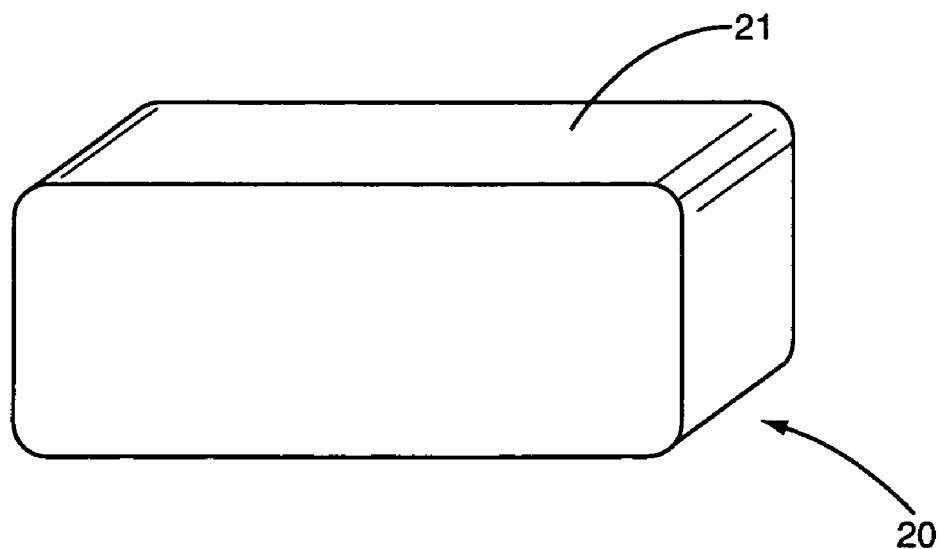
FIG. 26 is a perspective view illustrating an implant according to one embodiment.

The implant 20 may also be used in an interspinous context. FIGS. 2-4 illustrate embodiments of an interspinous implant 20 with opposing arms that form seats for positioning the spinous processes of the adjacent vertebral members 300. FIG. 25 illustrates another embodiment with less pronounced arms forming an indent to position the spinous processes. FIG. 26 illustrates an embodiment with substantially planar inferior and superior surfaces that are spaced apart a distance to support the spinous processes.

Various methods may be used during the insertion and positioning within the patient. One method includes the physician manually grasping the implant 20 and inserting it into the patient. The physician may also manipulate the implant 20 and position it within the patient.

Figure 27:
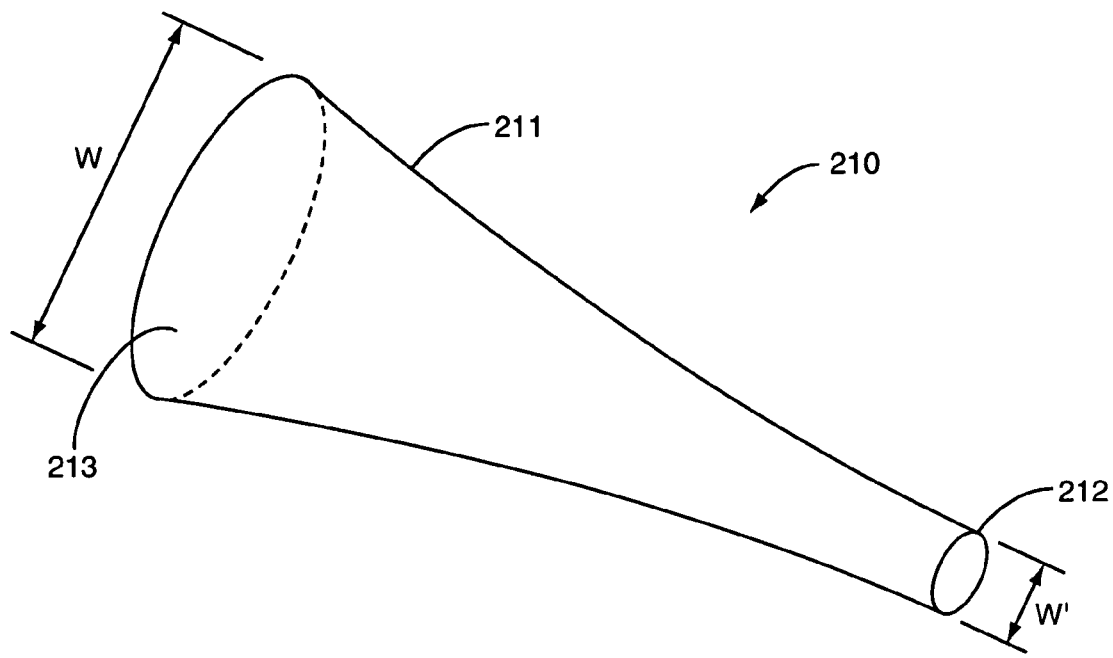
FIG. 27 is a perspective view illustrating a cannula according to one embodiment.

FIG. 27 illustrates a funneled cannula 210 that may be used during the process. The cannula 210 includes an enlarged proximal end 211 and a reduced distal end 212. An opening 213 extends through the length and decreases from a first width w at the proximal end 211 to a second reduced width w' at the distal end 212. The implant 20 is inserted into the proximal end 211 and moved through the cannula 210 thereby deforming it and reducing a cross-sectional size. The implant 20 is reduced in cross-sectional size upon exiting through the distal end 212. The cannula 210 may include a length to position the distal end 212 at the insert location within the patient with the proximal end 211 remaining on the exterior of the patient. The cannula 210 may be constructed of a rigid material, or may be flexible to facilitate insertion and positioning of the distal end 212 within the patient.

Figure 28:
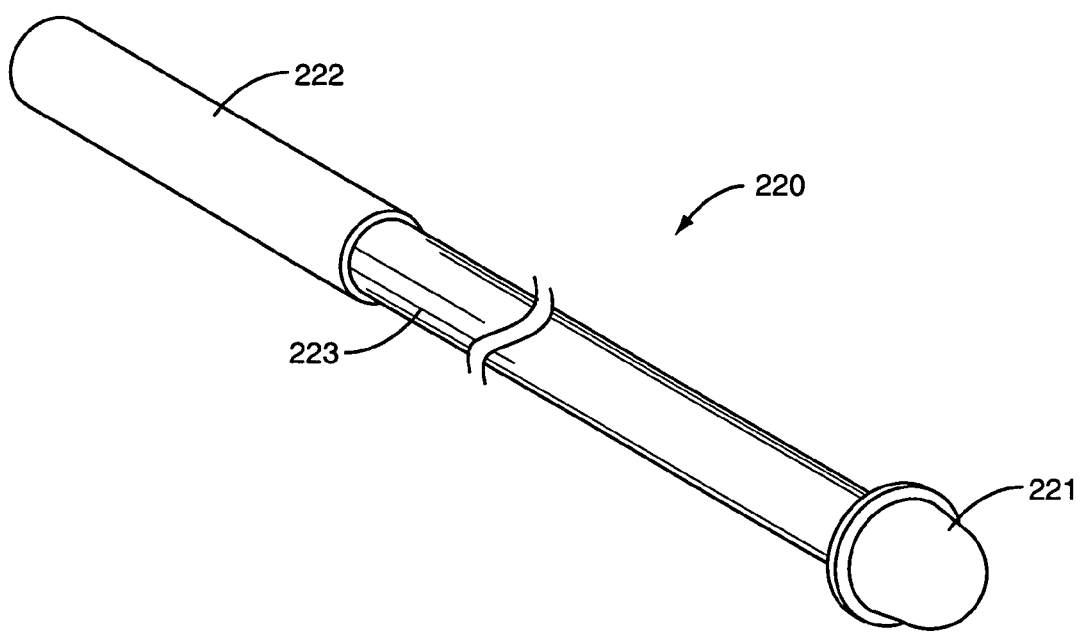
FIG. 28 is a side schematic view illustrating a plunger according to one embodiment.

In one embodiment, the implant 20 is moved through the cannula 210 by the fingers and hands of the physician. Another method may use a plunger 220 as illustrated in FIG. 28. Plunger 220 includes a shaft 223 that separates a head 221 and a handle 222. The head 221 is sized to fit within the opening 213 and through the distal end 212. The head 221 contacts the implant 20 and forces it through the length of the cannula 210 and into the patient. In one embodiment, head 221 is shaped to also position and mold the implant 20 when it is in the patient. In one embodiment, the head 221 is removable such that a first head moves the implant 20 through the cannula 221 and a second head is sized to mold and position the implant 20 once it has been delivered inside the patient. In another embodiment, a flexible member is tied to the implant 20. The flexible member extends through a section of the patient and exits from a second incision. The flexible wire may then be used to pull the implant 20 through the cannula 210 and into position within the patient.

Figure 29A:
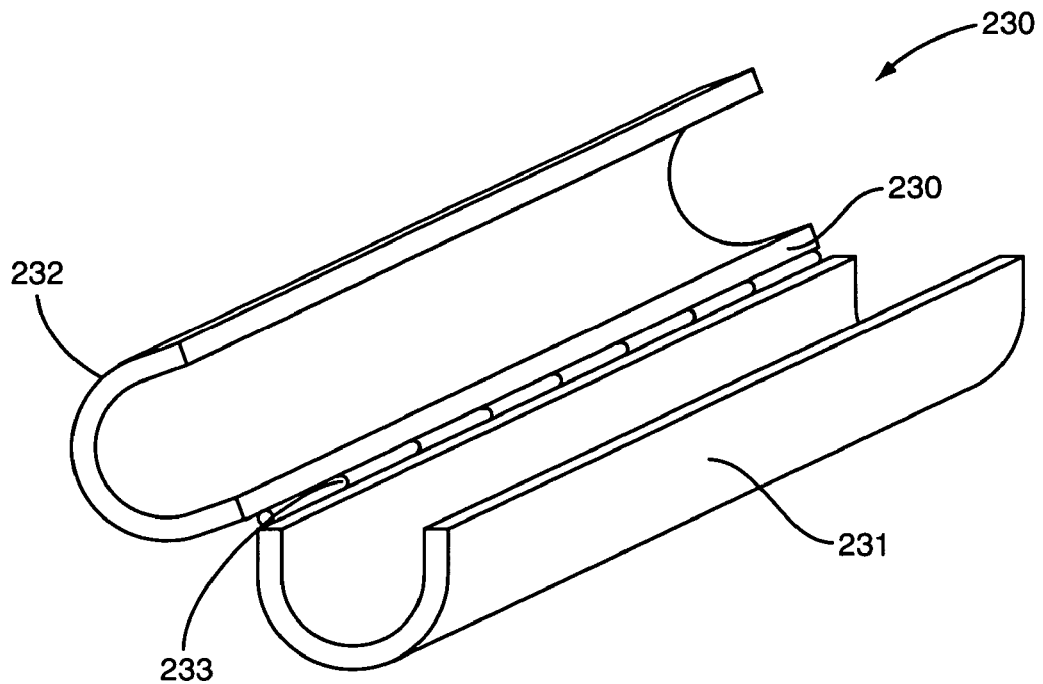
FIGS. 29A and 29B illustrate one embodiment of a cannula in first and second positions according to one embodiment.
Figure 29B:
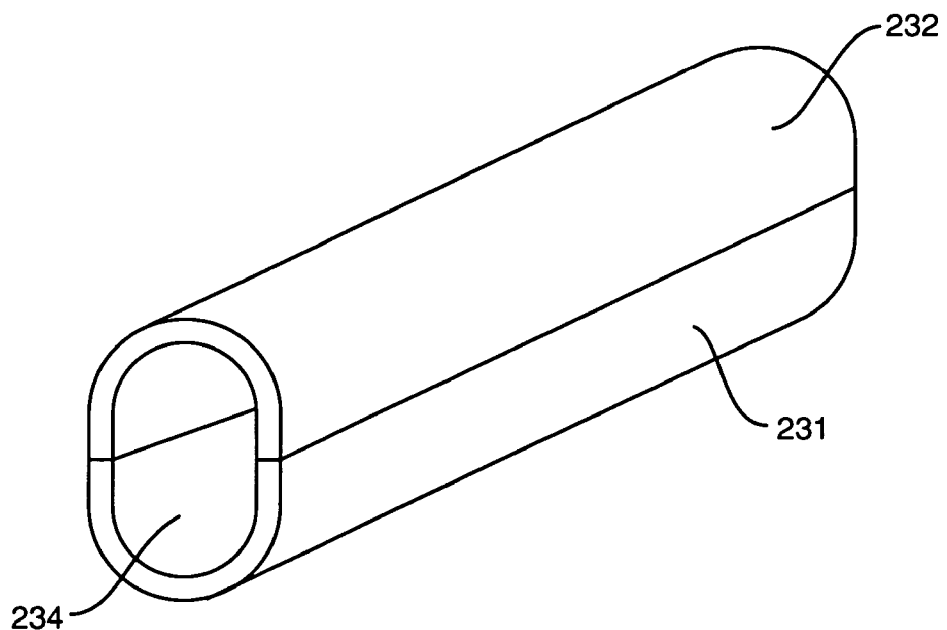

Another method may include a hinged cannula 230 as illustrated in FIGS. 29A and 29B. The cannula 230 includes a first section 231 and a second section 232 pivotally connected at one or more hinges 233. In the open orientation as illustrated in FIG. 29A, the interior of the cannula is exposed. In use, the implant 20 may be placed within the interior of the first or section sections 231, 232. This may require that the implant 20 be deformed to fit within this space. The two sections 231, 232 are than brought together in a closed orientation as illustrated in FIG. 29B. This movement may also deform the implant 20 and force it to fit within the interior space of the two sections 231, 232. The deformed implant 20 has a reduced cross-sectional size and may inserted into the patient in a manner as described above.

Figure 30A:
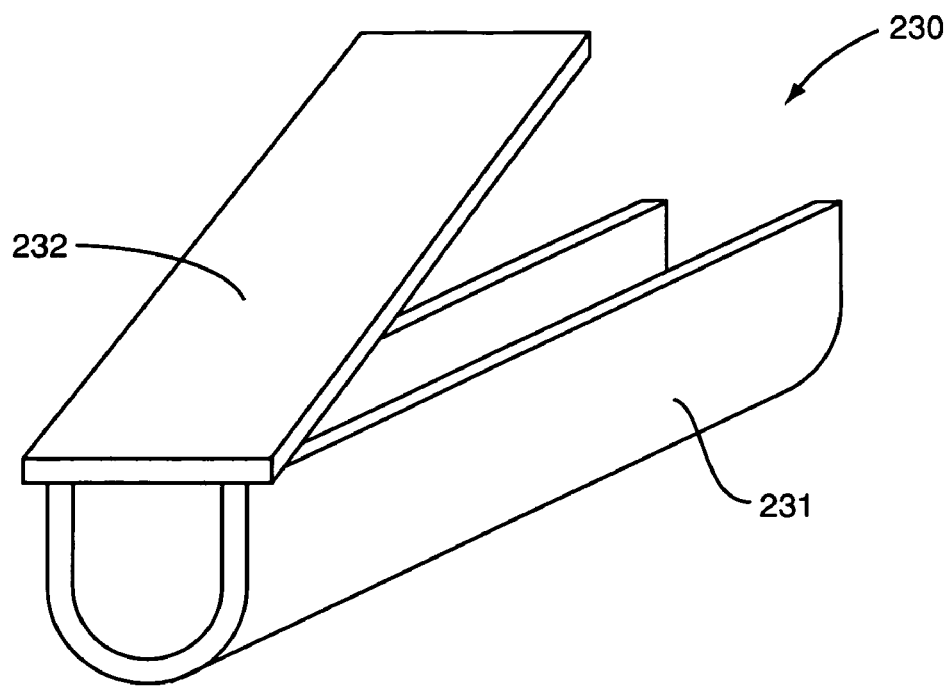
FIGS. 30A and 30B illustrate one embodiment of a cannula in first and second positions according to one embodiment.
Figure 30B:
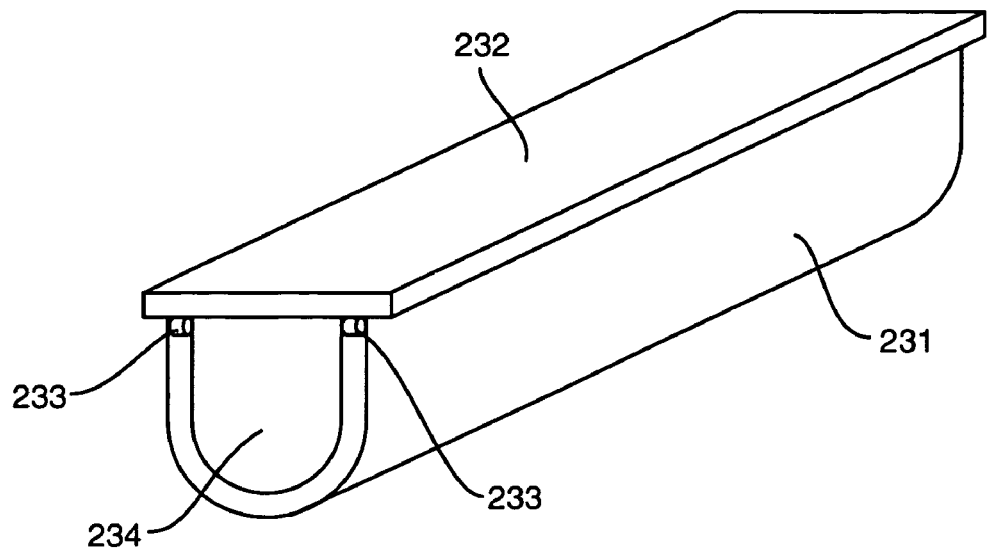

FIGS. 30A and 30B illustrate another embodiment of a hinged cannula 230. This embodiment includes one or more hinges 233 on the proximal end of the first and second sections 231, 232. In the open position as illustrated in FIG. 30A, the second section 232 lifts to expose the interior of the first section 231. The implant 20 may be deformed during insertion into the first section 231, and additional deformation may be occur when moving the second section 232 to the closed orientation. The implant 20 contained within the cannula 230 may be inserted into the patient as described above.

The first and second sections 231, 232 or the various cannula embodiments may be substantially the same, or may be different. FIGS. 29A and 29B illustrate an embodiment with the sections 231, 232 being substantially the same. FIGS. 30A and 30B include the sections including a different shape and size. In one embodiment, the sections 231, 232 include an overall funnel shape with the distal end including a smaller size than the proximal end to facilitate insertion into the patient.

In one embodiment, the material fills the shell 21 to an extent that the shell 21 inhibits the movement of the material. In one embodiment, shell 21 is non-compliant and the material completely fills the shell. This may reduce the overall malleability of the implant 20, and may prevent deformation to an extent that the implant 20 can be inserted in a minimally-invasive manner. In one embodiment, a portion of the material is removed from the shell 21 prior to or during insertion. The removal allows for the implant 20 to be more malleable and be deformed for insertion in a minimally invasive manner. The amount of material that is removed from the shell 21 may affect the overall malleability with a larger removal providing for greater deformation. In one embodiment, at least a portion of the material remains within the shell 21 during insertion. After the implant 20 is within the body, the material may be reintroduced into the shell 21. In one embodiment, a syringe 109 is inserted through an inlet 26 in the shell 21 to remove and reintroduce the material. The entire removed portion or a lesser amount may be replaced into the implant 20. Additional components may also be added to the implant 20.

Syringes 109 may be used in some embodiments to introduce one or more precursor materials into the shell 21. In other embodiments, a pump may be used to move the precursor material from a holding bin and into the shell 21.

The embodiments of the transformable implant 20 may be used for a variety of medical contexts. One context includes the spinal procedures including the cervical, thoracic, lumbar and/or sacral portions of the spine.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of supporting one or more vertebral members of a patient, the method comprising the steps of:
   rupturing a divider within an interior space of a shell;
   mixing and thereby activating a material within the interior space of the shell, the material including a first component that was previously contained within the interior space of the shell and isolated on a first side of the divider with a second component that was previously contained within the interior space of the shell and isolated on a second side of the divider, wherein mixing the material causes the material to start transforming from a non-load bearing state to a load bearing state;
   deforming the shell while the material is transforming, the deformation reducing the shell from a first configuration with an enlarged cross-sectional width to a second configuration with a reduced cross-sectional width; and
   inserting the shell and the material into the patient while in the second configuration while the material is transforming.

2. The method of claim 1, wherein rupturing the divider within the interior space of the shell includes rupturing a seal within the interior space of the shell and mixing the first component that was physically isolated on a first side of the seal with the second component that was physically isolated on a second side of the seal.

3. The method of claim 1, wherein rupturing the divider within the interior space of the shell includes rupturing a container within the interior space and mixing the first component that was isolated in the container from the second component.

4. The method of claim 3, wherein the step of rupturing the container comprises contacting the container with a rupture device positioned within the interior of the shell.

5. The method of claim 1, further comprising returning the shell towards the first configuration after inserting the shell and the material into the patient.

6. The method of claim 1, further comprising positioning the shell into an intervertebral space within the patient.

7. The method of claim 6, wherein the shell and the material form a fusion device.

8. The method of claim 6, wherein the shell and the material form a nucleus replacement device.

9. The method of claim 6, wherein the shell and the material form a disc prosthesis device.

10. The method of claim 1, further comprising positioning the shell into an interspinous space within the patient.

11. The method of claim 10, wherein the shell and the material form an interspinous spacer.

12. The method of claim 1, further comprising forming the shell into a rod.

13. The method of claim 12, wherein the shell and the material form a spinal rod that extends along the exterior of the one or more vertebral members.

14. The method of claim 1, further comprising forming the shell into a plate.

15. The method of claim 14, wherein the shell and the material form an anterior spinal plate.

16. The method of claim 1, further comprising transforming the material into a final rigid, solid state.

17. The method of claim 1, further comprising transforming the material into a final state that is flexible and forming a motion preserving device.

18. The method of claim 1, further comprising inserting one or more of a biological and a pharmaceutical agent through an aperture in the implant and into an opening in the implant.

19. The method of claim 1, further comprising positioning the shell within one of the vertebral members.

20. A method of supporting one or more vertebral members of a patient, the method comprising the steps of:
   activating a material contained within a shell and causing the material to start transforming from a non-solid non-load bearing state to a solid load bearing state;
   after activation and while the material is in the non-load bearing state, deforming the shell to a reduced cross-sectional width;
   after activation and while the material is in the non-load bearing state, inserting the shell into the patient; and
   supporting the vertebral members with the shell after the material transforms to the load bearing state;
   wherein the step of activating the material comprises mixing together first and second components.

21. The method of claim 20, wherein the step of activating the material within the shell includes rupturing a divider within the shell and mixing first and second components that were previously physically separated on different sides of the divider and positioned within the shell.

22. The method of claim 20, further comprising rupturing a container within the interior of the shell and mixing a first component that was isolated in the container with a second component contained within the shell.

23. The method of claim 20, wherein the step of deforming the shell to the reduced cross-sectional width comprises molding the shell and the material in a hinged cannula.

24. The method of claim 20, wherein the step of inserting the shell into the patient comprises forcing the shell and the material through a funneled cannula.

25. The method of claim 20, further comprising inserting one or more of a biological and a pharmaceutical agent through an aperture in the implant and into an opening in the implant.

26. A method of supporting one or more vertebral members of a patient, the method comprising the steps of:
   activating an implant and causing a material within the implant to start transforming from a malleable, non-load bearing state to a load bearing state;
   after activation and prior to transformation into the load bearing state, deforming a shell from a first cross-sectional configuration to a reduced second cross-sectional configuration;
   while in the second configuration, inserting the implant into the patient while the material is transforming and wherein the material continues to transform into the load bearing state while disposed within the patient; and
   supporting the vertebral members with the implant after the material transforms to the load bearing state;
   wherein the step of activating the implant comprises mixing first, second, and third components that were physically separated and positioned within a shell of the implant prior to the implant being activated.

27. The method of claim 26, wherein the step of activating the implant comprises rupturing a seal that physically separates first and second components and mixing together the first and second components, the components being positioned within the implant prior to the implant being activated.

28. The method of claim 26, wherein the step of activating the implant comprises rupturing a container that contains a second component and mixing together the second component and a first component that is within a shell of the implant.

29. The method of claim 26, further comprising inserting one or more of a biological and a pharmaceutical agent through an aperture in the implant and into an opening in the implant.

30. The method of claim 26, wherein the step of inserting the implant into the patient comprises engaging teeth on the implant with the vertebral members.

31. The method of claim 26, wherein the step of inserting the implant into the patient comprises positioning the implant between opposing support plates that are each in contact with one of the vertebral members.

32. The method of claim 26, wherein the step of inserting the implant into the patient comprises positioning the implant within anchors that are attached to and extend outward from the vertebral members.

33. The method of claim 32, further comprising forming the implant into a rod after insertion into the patient.

34. The method of claim 26, wherein the step of inserting the implant into the patient comprises positioning the implant between spinous processes of the vertebral members.

35. The method of claim 26, wherein the step of inserting the implant into the patient comprises positioning the implant into an intervertebral space within the patient.

36. The method of claim 26, wherein the step of deforming the shell from the first configuration to the reduced second configuration comprises forcing the implant through a funneled cannula and into the patient.

37. The method of claim 36, wherein the step of deforming the shell from the first configuration to the reduced second configuration comprises inserting the implant into a first section of a hinged cannula and moving a second section to a closed orientation.

38. The method of claim 26, further comprising visually observing a change in appearance of the material after activation.

39. The method of claim 26, further comprising tactilely feeling a change in hardness of the material after activation.

40. The method of claim 26, further comprising transforming the material into a final rigid, solid state and forming a fusion device.

41. The method of claim 26, further comprising transforming the material into a final state that is flexible and forming a motion preserving device.

42. The method of claim 26, further comprising positioning the shell within one of the vertebral members.

43. A method of supporting one or more vertebral members of a patient, the method comprising the steps of:
 physically separating a first component within a shell from a second component within the shell;
 rupturing a seal within the shell that physically separates the first and second components;
 mixing together the first and second components and forming an activated material;
 positioning the implant within the patient while the activated material is transforming from a non-load bearing state to a load bearing state; and
 supporting the vertebral members with the implant after the activated material transforms to the load bearing state.

44. The method of claim 43, wherein the step of rupturing the seal that physically separates the first and second components comprises physically deforming the shell.

45. The method of claim 43, wherein the step of rupturing the seal that physically separates the first and second components comprises contacting the seal against a rupture device that is positioned within the shell.

46. The method of claim 1, wherein an amount of material within the shell is the same before and after activation.

47. The method of claim 1, wherein the activation occurs without adding additional material within the shell.

48. The method of claim 47, wherein the volume of the shell increases during transformation.

49. The method of claim 1, wherein the shell is portless.

50. The method of claim 20, wherein an amount of material within the shell is the same before and after activation.

51. The method of claim 20, wherein the activation occurs without adding additional material within the shell.

52. The method of claim 51, wherein the volume of the shell increases during transformation.

53. The method of claim 20, wherein the shell is portless.

54. The method of claim 26, wherein an amount of material within the implant is the same before and after activation.

55. The method of claim 26, wherein the activation occurs without adding additional material within the implant.

56. The method of claim 55, wherein the volume of the implant increases during transformation.

57. The method of claim 26, wherein the implant is portless.

* * * * *